(12) United States Patent
Nakamura et al.

(10) Patent No.: US 7,771,368 B2
(45) Date of Patent: Aug. 10, 2010

(54) BODY FLUID COLLECTING DEVICE

(75) Inventors: Toshihisa Nakamura, Kanagawa (JP); Yoshiaki Yaguchi, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1355 days.

(21) Appl. No.: 10/519,790

(22) PCT Filed: Jun. 30, 2003

(86) PCT No.: PCT/JP03/08310

§ 371 (c)(1),
(2), (4) Date: Sep. 22, 2005

(87) PCT Pub. No.: WO2004/002312

PCT Pub. Date: Jan. 8, 2004

(65) Prior Publication Data

US 2006/0116607 A1     Jun. 1, 2006

(30) Foreign Application Priority Data

Jul. 1, 2002 (JP) ............................. 2002-192773
Jul. 1, 2002 (JP) ............................. 2002-192774

(51) Int. Cl.
*A61B 5/00* (2006.01)
*B65D 81/00* (2006.01)

(52) U.S. Cl. ...................................... 600/584; 600/583
(58) Field of Classification Search .................. 600/345, 600/573, 583, 584
See application file for complete search history.

(56) References Cited

U.S. PATENT DOCUMENTS

| 6,093,156 | A | 7/2000 | Cunningham et al. |
| 6,315,738 | B1 | 11/2001 | Nishikawa et al. |
| 6,506,168 | B1 * | 1/2003 | Fathallah et al. ............ 600/578 |
| 7,264,627 | B2 * | 9/2007 | Perez ........................ 606/181 |
| 2002/0198444 | A1 | 12/2002 | Uchigaki et al. |
| 2003/0109808 | A1 | 6/2003 | Takinami et al. |

FOREIGN PATENT DOCUMENTS

| EP | 0 988 828 A1 | 3/2000 |
| EP | 1 174 083 A2 | 1/2002 |
| JP | 2000-116626 | 4/2000 |

(Continued)

OTHER PUBLICATIONS

Supplementary Partial European Search Report.

(Continued)

*Primary Examiner*—Max Hindenburg
*Assistant Examiner*—Jonathan M. Foreman
(74) *Attorney, Agent, or Firm*—Buchanan Ingersoll & Rooney PC

(57) ABSTRACT

A body fluid collecting device which is easy to operate to collect body fluid and which is capable of detecting specific components in body fluid with a small amount of sample includes a sensor to detect a prescribed component in the body fluid, and a first supporter to support the vicinity of the measuring part of the sensor and a second supporter to support the sensor at a place closer to the proximal end than the first supporter. The first and second supporters form between them a non-contact space, wherein the first supporter has at its proximal end a concave that communicates with the non-contact space.

10 Claims, 10 Drawing Sheets

FOREIGN PATENT DOCUMENTS

| | | |
|---|---|---|
| JP | 2000-217804 | 8/2000 |
| JP | 2001-74731 | 3/2001 |
| JP | 2002-34956 | 2/2002 |
| JP | 2002-58661 A | 2/2002 |
| JP | 2002-085384 | 3/2002 |
| JP | 2003-180663 | 7/2003 |
| WO | WO 00/40150 A1 | 7/2000 |
| WO | 01/41643 A1 | 6/2001 |
| WO | WO 02/07599 A | 1/2002 |

OTHER PUBLICATIONS

Supplementary European Search Report.

* cited by examiner

F I G. 4
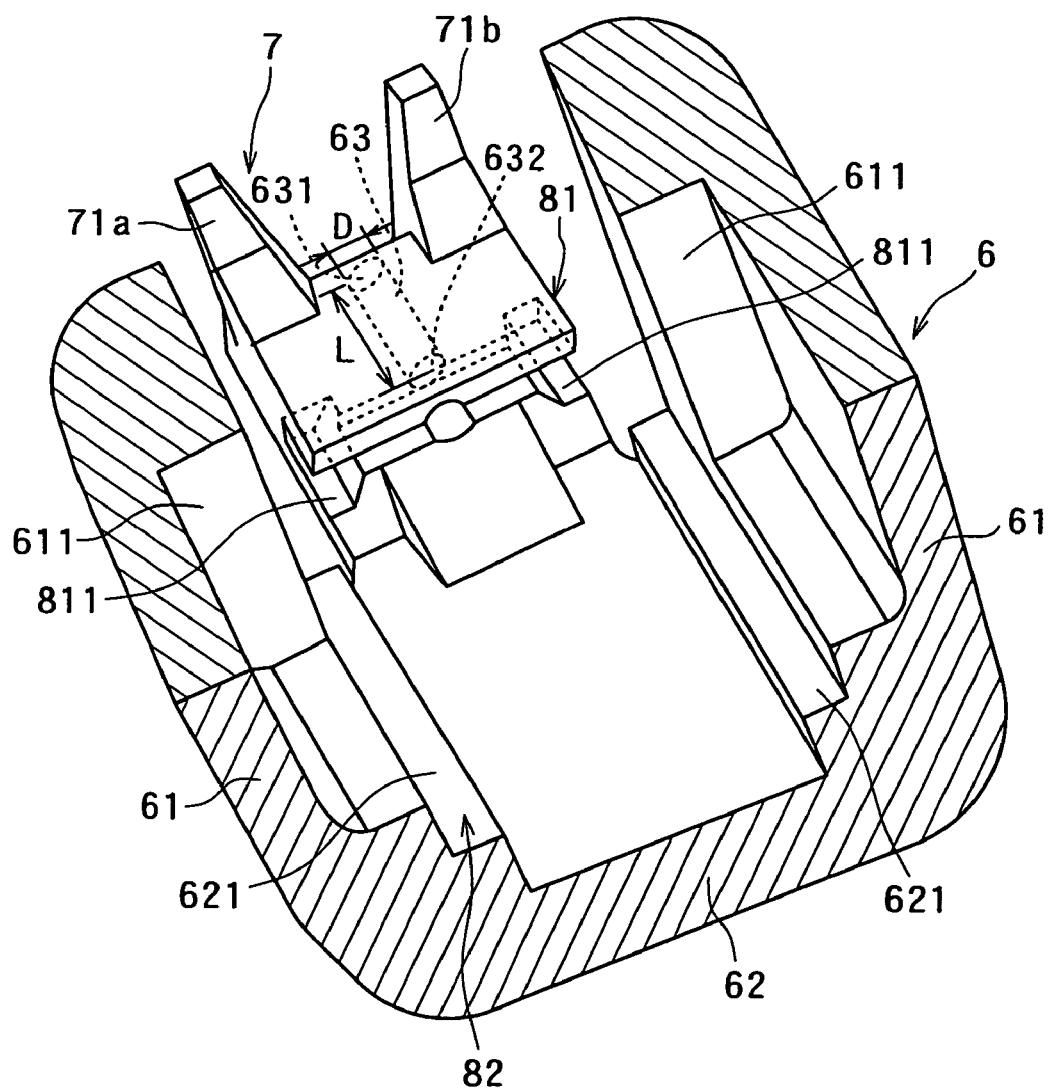

BODY FLUID COLLECTING DEVICE

This application claims priority on Japanese patent application Nos. 2002-192773 and 2002-192774, the entire contents of which are hereby incorporated by reference. In addition, the entire content of literature cited in this specification are incorporated by reference.

TECHNICAL FIELD

The present invention relates to a body fluid collecting device to be mounted on an apparatus for measuring components, such an apparatus for measuring the blood glucose level.

BACKGROUND ART

There have been proposed several methods for determining various components in blood, particularly by analyzing the reaction products resulting from reaction between specific components in blood and specific enzymes. Measurement of blood glucose level is important to monitor the patient's status. It has been recommended that the patient measures his own blood glucose level every day by himself. In view of the recent increasing number of diabetics, there is a growing demand for a simple method and means of measuring blood glucose level with a minimum of pain.

Measurements of blood glucose level are usually accomplished by utilizing the enzymatic reaction to oxidize glucose. The enzymes for this purpose are glucose oxidase, glucose dehydrogenase, and the like. At present, colorimetric and electrical methods are used for determination of blood glucose level. The former method consists of attaching an indicator paper to a measurement device, introducing blood sample to the indicator paper which develops a color upon reaction with blood glucose and optically measuring the thus developed color. The latter method consists of measuring the amount of current flowing across electrodes in contact with the product resulting from enzymatic reaction.

What is essential for these methods is to collect blood samples for analysis. Before measurement, the patient has to collect his own blood. A common way to achieve this object is by sticking the patient's skin (that of the fingertip, for example) with a sticking device provided with a sticking needle and then squeezing out blood by pressing with fingers the surrounding of the point of sticking.

Unfortunately, the conventional optical measuring method using the indicator paper requires a comparatively large amount of blood and hence necessitates sticking the needle deep into the skin. This causes pain to the patient and intimidates many patients into giving up a self measurement of blood glucose level. This holds true for the electrical measuring method which also requires as much blood as the calorimetric method.

The conventional sensor used to electrically measure blood glucose level is usually composed of an insulating substrate or sheet, carbon or metal electrodes formed thereon by screen printing or the like, and a layer that absorbs blood dropped thereon. The layer contains an enzyme, electron acceptor, and electrolyte for pH adjustment. Many of the sensors are in the form of thin strip chip. In these sensors, the layer to absorb blood is formed at the distal end or side of the strip, so that it is given a blood sample directly. This structure presents difficulties in accurately placing a blood drop or tends to cause a failure.

If the sensor in strip form is integrated with a sticking needle, then the resulting device obviates the necessity of mounting the sticking needle and the sensor separately. This will simplify operation and improve usability. This idea, however, poses a problem of making it difficult to delicately adjust the sticking depth, which is the fatal cause for pain due to sticking.

Moreover, the device of integral type is complex in structure and tends to waste blood infiltrating into gaps between constituent members.

DISCLOSURE OF THE INVENTION

It is an object of the present invention to provide a body fluid collecting device which is easy to operate to collect body fluid and which is capable of detecting specific components in body fluid with a small amount of sample. It is another object of the present invention to provide a body fluid collecting device of the type integral with a sticking needle, which permits easy control of sticking depth. It is still another object of the present invention to provide a body fluid collecting device of the type integral with a sticking needle, which surely detects specific components in body fluid.

The above-mentioned objects are achieved by the invention defined in the following paragraphs (1) to (27).

(1) A body fluid collecting device having a sensor to detect a prescribed component in the body fluid, characterized in that the sensor has at its distal end a measuring part capable of holding the body fluid, and the body fluid collecting device has a first supporter to support the vicinity of the measuring part of the sensor and a second supporter to support the sensor at a place closer to the proximal end than the first supporter and also has means to prevent the body fluid from infiltrating into other parts than the measuring part.

(2) A body fluid collecting device having a sensor to detect a prescribed component in the body fluid, characterized in that the sensor has at its distal end a measuring part capable of holding the body fluid, and the body fluid collecting device has a first supporter to support the vicinity of the measuring part of the sensor and a second supporter to support the sensor at a place closer to the proximal end than the first supporter, with the first and second supporters forming between them a non-contact space in which the surface of the sensor does not substantially come into contact with the inside of the body fluid collecting device.

(3) The body fluid collecting device as defined in Paragraph (2), wherein the first supporter has at its proximal end a concave that communicates with the non-contact space.

(4) The body fluid collecting device as defined in Paragraph (3), wherein the concave is a notch formed by cutting part of the first supporter.

(5) The body fluid collecting device as defined in any of Paragraphs (2) to (4), wherein the sensor is bent or curved in the non-contact space.

(6) The body fluid collecting device as defined in any of Paragraphs (1) to (5), wherein the first supporter is arranged closer to the central axis of the body fluid collecting device than the second supporter.

(7) The body fluid collecting device as defined in any of Paragraphs (1) to (6), which further has a body fluid duct which communicates with the first supporter and introduces the body fluid into the measuring part.

(8) The body fluid collecting device as defined in Paragraph (7), wherein the body fluid duct has a volume which is 0.5 to 2 times the volume of the measuring part.

(9) The body fluid collecting device as defined in Paragraph (7) or (8), wherein the body fluid duct is 0.1 to 10 mm in length and 0.1 to 3 mm in inside diameter.

(10) The body fluid collecting device as defined in any of Paragraphs (7) to (9), wherein the measuring part is inclined with respect to the lengthwise direction of the body fluid duct and is positioned in the vicinity of the outlet opening of the body fluid duct.

(11) The body fluid collecting device as defined in any of Paragraphs (7) to (10), which further has a guide that projects from the distal end of the body fluid collecting device and introduces the body fluid into the inlet opening of the body fluid duct, the guide being formed such that the distance from the distal end thereof to the inlet opening of the body fluid duct is 1 to 10 mm.

(12) The body fluid collecting device as defined in any of Paragraphs (1) to (11), wherein the sensor electrically detects the prescribed component in the body fluid by contact with the body fluid.

(13) A body fluid collecting device of the type integral with a sticking needle which includes:

a needle accommodating part provided with a sticking needle which sticks the skin to bleed body fluid, a sensor to detect prescribed components in the body fluid, and a sensor holder which is mounted on the distal end of the needle accommodating part and which supports the sensor between the needle accommodating part and the sensor holder.

(14) The body fluid collecting device of the type integral with a sticking needle as defined in Paragraph (13), wherein the sensor has its distal end side curved or inclined toward the central axis of the sticking needle.

(15) The body fluid collecting device of the type integral with a sticking needle as defined in Paragraph (13) or (14), wherein the sensor has its proximal end side held between the needle accommodating part and the sensor holder.

(16) The body fluid collecting device of the type integral with a sticking needle as defined in any of Paragraphs (13) to (15), wherein the sensor is capable of holding the body fluid in its distal end and is provided with a measuring part to determine the prescribed components.

(17) The body fluid collecting device of the type integral with a sticking needle as defined in Paragraph (16), wherein the sensor holder has a body fluid duct which introduces the body fluid into the measuring part.

(18) The body fluid collecting device of the type integral with a sticking needle as defined in Paragraph (17), wherein the measuring part is inclined with respect to the lengthwise direction of the body fluid duct and is positioned in the vicinity of the outlet opening of the body fluid duct.

(19) The body fluid collecting device of the type integral with a sticking needle as defined in Paragraph (17) or (18), wherein the sensor holder has a guide that projects from the distal end thereof and introduces the body fluid into the inlet opening of the body fluid duct, so that the sticking needle sticks into the skin while the distal end of the guide is in contact with the skin.

(20) The body fluid collecting device of the type integral with a sticking needle as defined in any of Paragraphs (13) to (19), wherein the sensor holder is fixed by fitting to the needle accommodating part.

(21) The body fluid collecting device of the type integral with a sticking needle as defined in any of Paragraphs (13) to (20), which further has means to position the sensor holder with respect to the lengthwise direction of the needle accommodating part.

(22) The body fluid collecting device of the type integral with a sticking needle as defined in Paragraph (21), wherein the positioning means is a step that is formed on the outside midway in the lengthwise direction of the needle accommodating part such that the proximal end of the sensor holder comes into contact with it.

(23) The body fluid collecting device of the type integral with a sticking needle as defined in any of Paragraphs (13) to (22), wherein the sensor holder has at least the distal end thereof made substantially transparent.

(24) The body fluid collecting device of the type integral with a sticking needle as defined in any of Paragraphs (13) to (23), which is assembled after the needle accommodating part has undergone sterilization in such a state that its opening is sealed with a membrane, the opening being formed at the distal end of the needle accommodating part such that the sticking needle can pass through it.

(25) The body fluid collecting device of the type integral with a sticking needle as defined in Paragraph (24), wherein the needle accommodating part keeps its inside sterilized until the time of use.

(26) The body fluid collecting device of the type integral with a sticking needle as defined in any of Paragraphs (13) to (25), which assumes approximately a rectangular solid in its entire shape.

(27) The body fluid collecting device of the type integral with a sticking needle as defined in any of Paragraphs (13) to (26), wherein the sensor electrically detects the prescribed component in the body fluid by contact with the body fluid.

BRIEF DESCRIPTION OF THE DRAWINGS

FIG. 4 is a bottom view of the distal end of the sensor holder installed in the fluid body collecting device shown in FIG. 1.

BEST MODE FOR CARRYING OUT THE INVENTION

<Component Measuring Apparatus>

The body fluid collecting device according to the present invention is mounted on a device for measuring components when it is in use. The latter will be explained first with reference to FIGS. 8 to 10. In the following description, it is assumed that the apparatus is intended to collect body fluid (typically blood) through the skin and measure (detect) specific components in the collected body fluid.

It is desirable to collect body fluid through the skin of the finger; however, it is also possible to collect body fluid through the skin of the hand (palm, back, or side), arm, thigh, or ear lobe. In the following description, it is assumed that the apparatus is so designed as to collect body fluid by sticking the fingertip.

Figure 8:
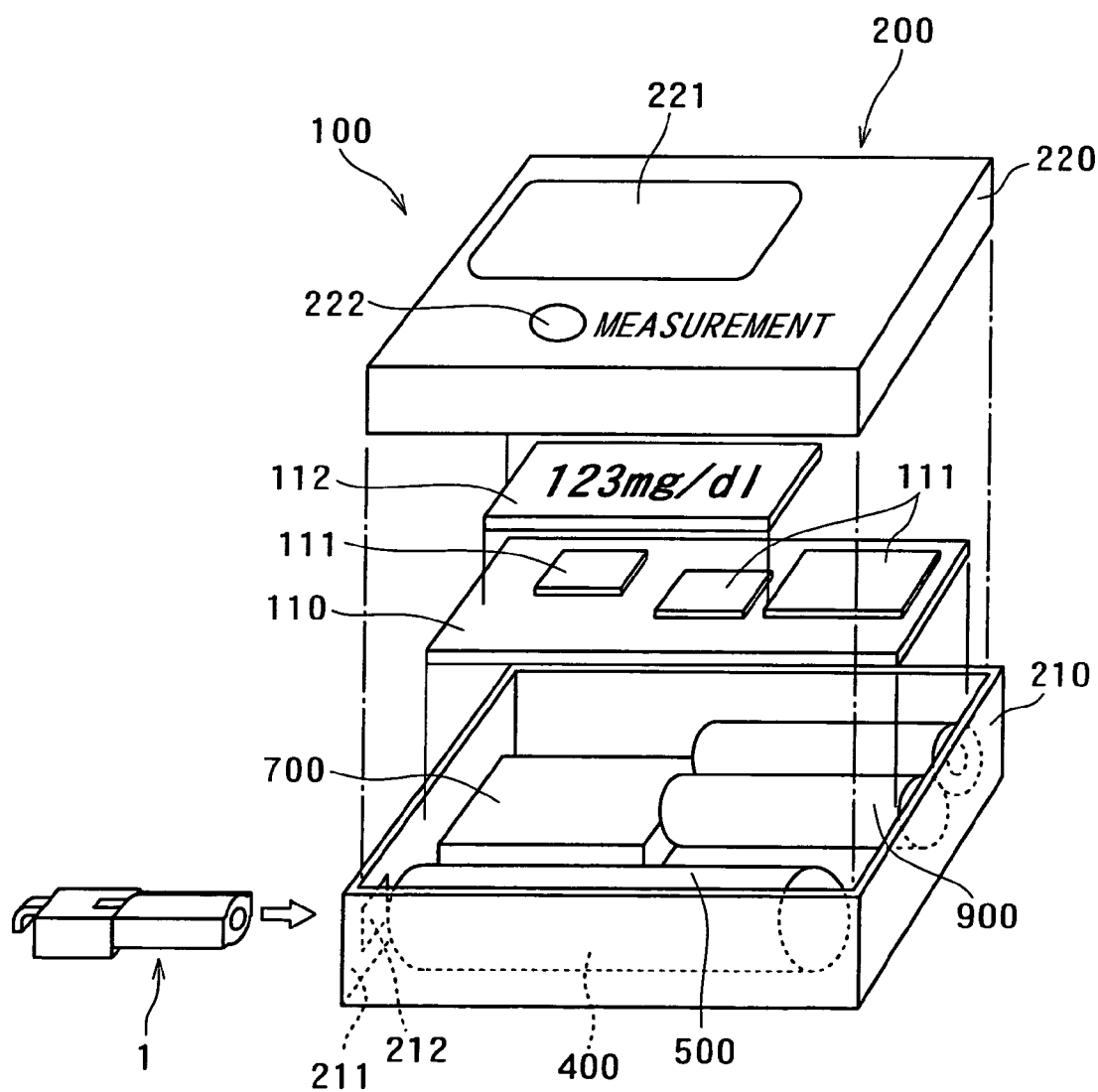
FIG. 8 is a schematic exploded perspective view of the component measuring apparatus on which is mounted the body fluid collecting device according to the present invention.
Figure 9:
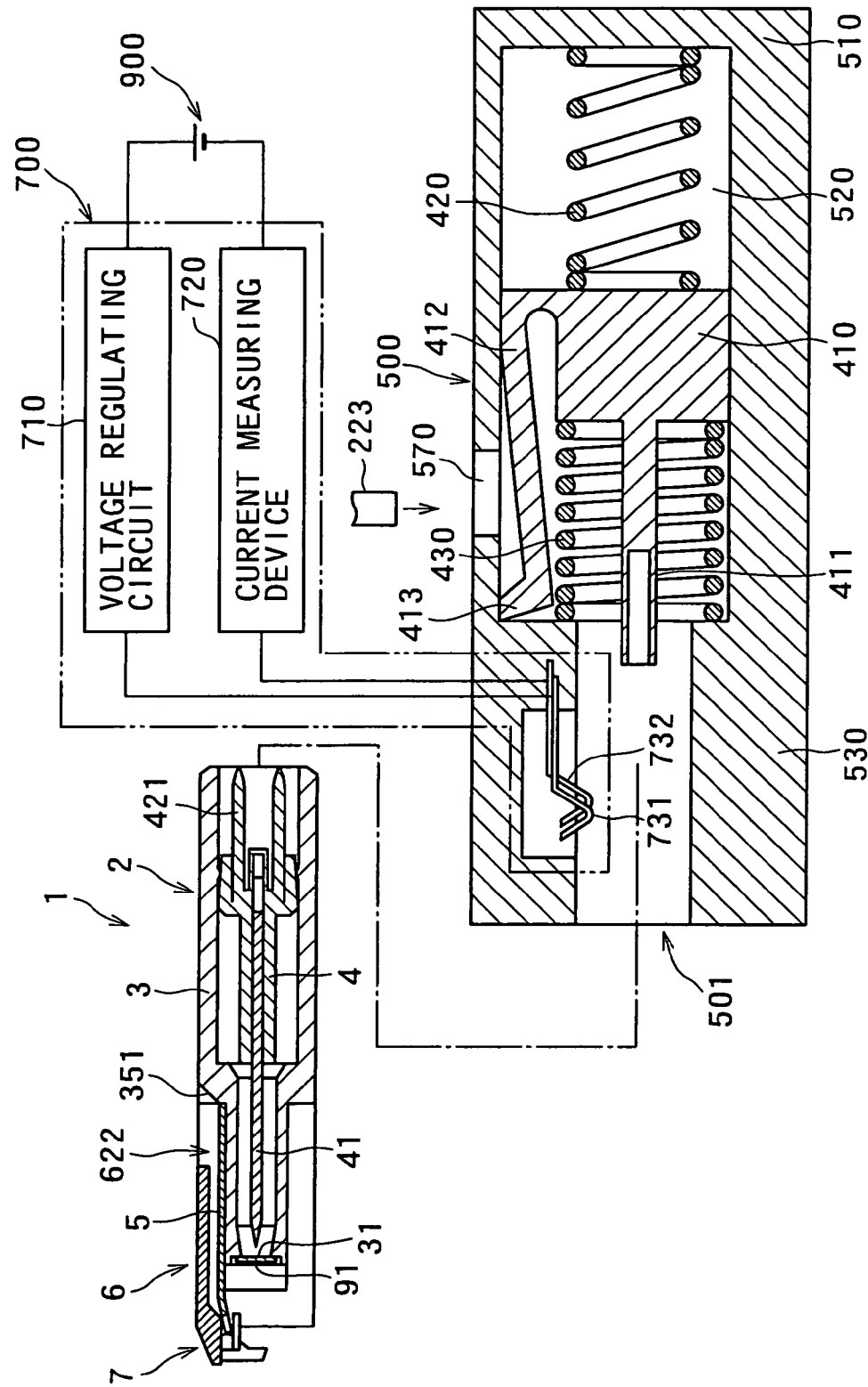
FIG. 9 is a schematic diagram (partly in section) showing how the component measuring apparatus shown in FIG. 8 is made up of a housing, sticking means, and measuring means.
Figure 10:
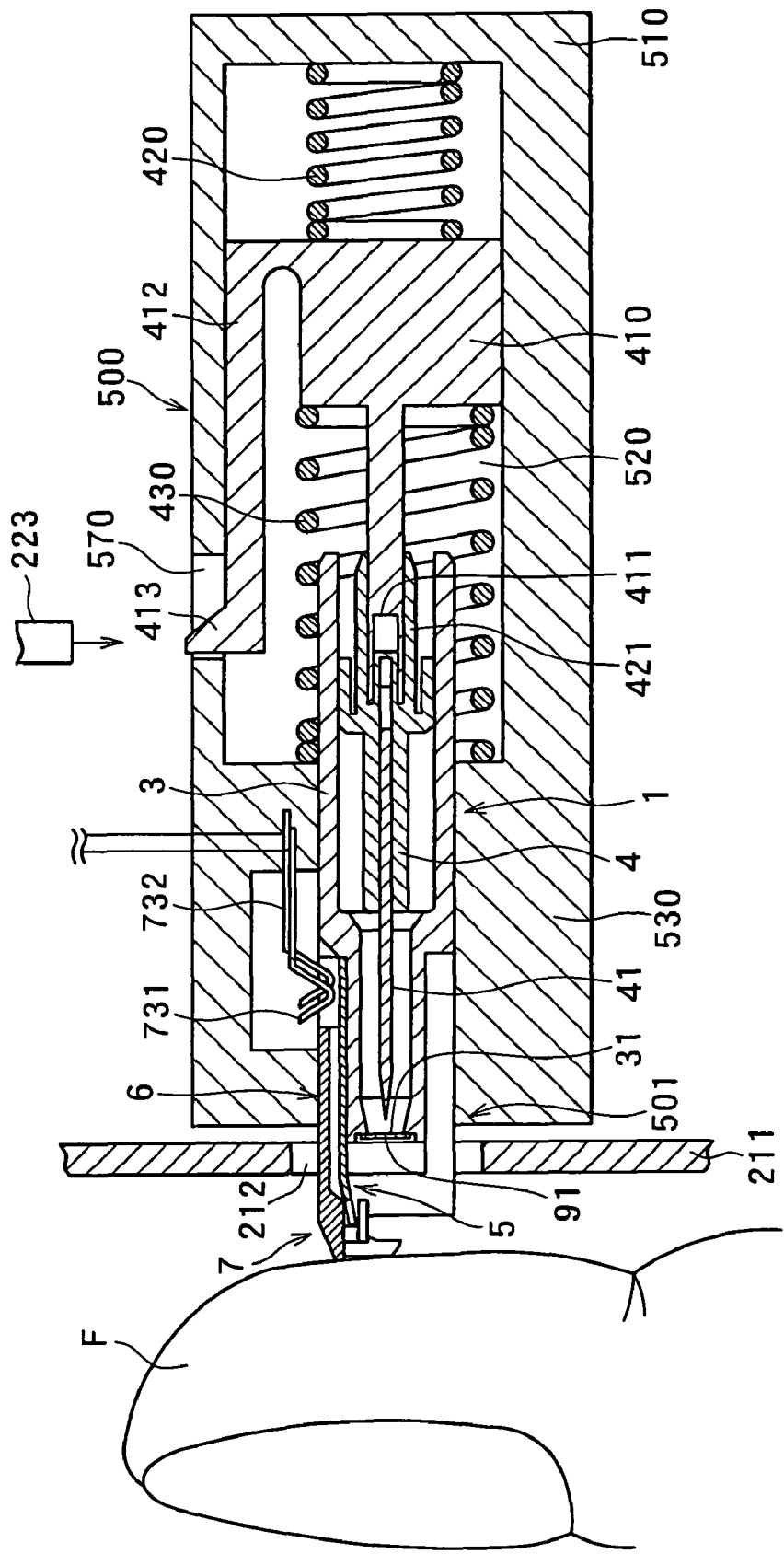
FIG. 10 is a schematic diagram (partly in section) showing how the component measuring apparatus shown in FIG. 8 is made up of a housing, sticking means, and measuring means.

FIG. 8 is a schematic exploded perspective view of the component measuring apparatus on which is mounted the body fluid collecting device according to the present invention. FIGS. 9 and 10 are schematic diagrams (partly in section) showing how the component measuring apparatus shown in FIG. 8 is made up of a housing, sticking means, and measuring means. Incidentally, conventions are adopted as follows in the following description. "Proximal end", "distal end", "up", "down" represent respectively the right side, the left side, the upper side, and the lower side in FIGS. 8 to 10.

The component measuring apparatus (or the blood component measuring apparatus) 100 shown in FIG. 8 includes a main body 200, a housing 500 holding a sticking means 400, a measuring means 700, a power source (batteries) 900, a circuit board 110 and a control means 111 mounted thereon, and a display unit 112. The measuring means 700 is designed to measure (detect) a specific component (typically glucose in this embodiment) in the collected blood (body fluid). The component measuring apparatus 100 is designed such that the body fluid collecting device 1 according to the present invention is fixed in the distal end of the housing 500.

The constituents of the apparatus 100 will be described one by one in the following.

The main body 200 includes a casing 210 and a lid 220 and contains the constituents mentioned above.

The wall 211 at the distal end of the casing 210 has an approximately by rectangular opening 212 (conforming to the cross section of the body fluid collecting device 1 mentioned later) penetrating the wall of the casing 210. The body fluid collecting device 1 is fitted into the distal end of the housing 500 through the opening 212.

In the lid 220, an opening (window) 221 closed by a transparent sheet is formed, and penetrates the lid 220.

The display unit 112 is installed at that part in the main body 200 which corresponds to the window 221. Thus the window 221 permits the user to see through it various kinds of information displayed on the display unit 112.

The display unit 112 consists of liquid crystal display elements (LCDs) or the like. It displays such information as power on/off, power source voltage (remaining capacity), measured values, date and time of measurement, error indication, and operation guidance.

On the lid 220 is arranged a control button 222, the depressing of which actuates the sticking means 400 mentioned later.

The control means 111 controls the actions of each part in the component measuring apparatus 100. It is also provided with an arithmetic section to calculate the blood glucose level in response to signals from the measuring means 700.

The battery 900 supplies the control means 111, the display unit 112, and the measuring means 700 with electric power for their operation through electric connections.

The casing 210 has an opening 212 which corresponds to the distal opening 501 of the housing 500.

As shown in FIGS. 9 and 10, the housing 500 is a cylindrical member having a bottom 510 and an internal space 520 for accommodation.

At the distal end of the housing 500, a holder 530 which has an internal shape formed corresponding to an external shape of the body fluid collecting device 1 is formed. Into the holder 530, the body fluid collecting device 1 snugly fits.

The sticking means 400 is held in the internal space 520 in the proximal side of the holder 530. The sticking means 400 is so designed as to move distally the sticking needle 4 which is held by the needle holder 411. The sticking needle 4 has a needle body 41 having a sharp needle point, which sticks into the skin of the fingertip F.

The sticking means 400 includes a plunger 410, a coil spring 420 to urge the plunger 410 toward the distal end, and a coil spring 430 to urge the plunger 410 toward the proximal end.

The plunger 410 has an integrally formed cup-like needle holder 411 at its distal end. This needle holder 411 detachably holds the fitting part 421 of the sticking needle 4.

The plunger 410 has an integrally formed elastic piece 412, which can deform elastically, extending from its proximal end. This elastic piece 412 has a locking part 413 projecting from its distal end. It deflects up and down about its proximal end so that the locking part 413 moves up and down, as shown in FIGS. 9 and 10.

The top of the locking part 413 is in contact with the inside of the housing 500 due to the elastic force of the elastic piece 412 before the body fluid collecting device 1 is held in the housing 500 (or before the sticking needle 4 is held by the needle holder 411 of the plunger 410), as shown in FIG. 9. On the other hand, after the body fluid collecting device 1 has been held in the housing 500 (or after the sticking needle 4 has been held by the needle holder 411 of the plunger 410), the locking part 413 enters the opening 570 formed in the side wall of the housing 500 and locked at the edge of the opening 570, as shown in FIG. 10. Thus the plunger 410 is restrained from moving forward.

The coil spring (for sticking) 420 extends from the plunger 410 toward the proximal end side, so that its both ends are in contact with the plunger 410 and the wall 510. On the other hand, the coil spring (for return) 430 extends from the distal end of the plunger 410, so that its both ends are in contact with the plunger 410 and the holder 530.

As shown in FIGS. 9 and 10, outside the housing 500 is an unlocking part 223, which pushes the locking part 413 toward the internal space 520 (or in the direction of arrow). This unlocking part 223 is actuated as the control button 222 (mentioned above) is depressed.

While the locking part 413 is in engagement with the edge of the opening 570 (as shown in FIG. 10), the coil spring 420 is compressed to urge the plunger 410 toward the distal end. As the unlocking part 223 is moved in the direction of arrow and the locking part 413 is unlocked (as shown in FIG. 10), the coil spring 420 extends to move the plunger 410 toward the distal end. As the result, the sticking needle 4 is moved toward the distal end, so that the tip of the needle body 41 sticks into the skin of the fingertip F. In this state, the coil spring 430 is compressed.

Then, the coil spring 430 pushes back the plunger 410 toward the proximal end. The plunger 410 reciprocates (or repeatedly moves toward the distal end and toward the proximal end) due to elastic force applied by the coil springs 420 and 430. It eventually comes to rest at a position where the force of the coil spring 420 balances with that of the coil spring 430.

While the plunger 410 is at rest, the tip of the needle body 41 (fixed to the sticking needle 4) is accommodated in the body fluid collecting device 1.

The measuring means 700 includes a voltage regulating circuit 710 (which applies a prescribed voltage to the sensor 5 of the body fluid collecting device 1), a current measuring device 720 for measuring a current value, and contact points 731 and 732 (which come into contact with the electrodes 52a and 52b of the sensor 5).

The contact point 731 is electrically connected to the battery 900 through the voltage regulating circuit 710, and the contact point 732 is electrically connected to the battery 900 through the current measuring device 720.

The measuring means 700 measures (detects), by means of the current measuring device 720, change in the current which the sensor 5 outputs according to the amount of glucose in blood, and it sends the detected signals to the control means 111.

The control means (arithmetic unit) 111 performs prescribed computing in response to input signals and also optionally performs calibration, thereby determining the blood glucose level. The thus determined blood glucose level is displayed on the display unit 112.

On the component measuring apparatus 100 mentioned above is mounted the body fluid collecting device 1 according to the present invention.

<Body Fluid Collecting Device>

A detailed description is given below of the body fluid collecting device according to the present invention.

First Embodiment

The first embodiment of the present invention covers the body fluid collecting device integral with the sticking needle.

Figure 1:
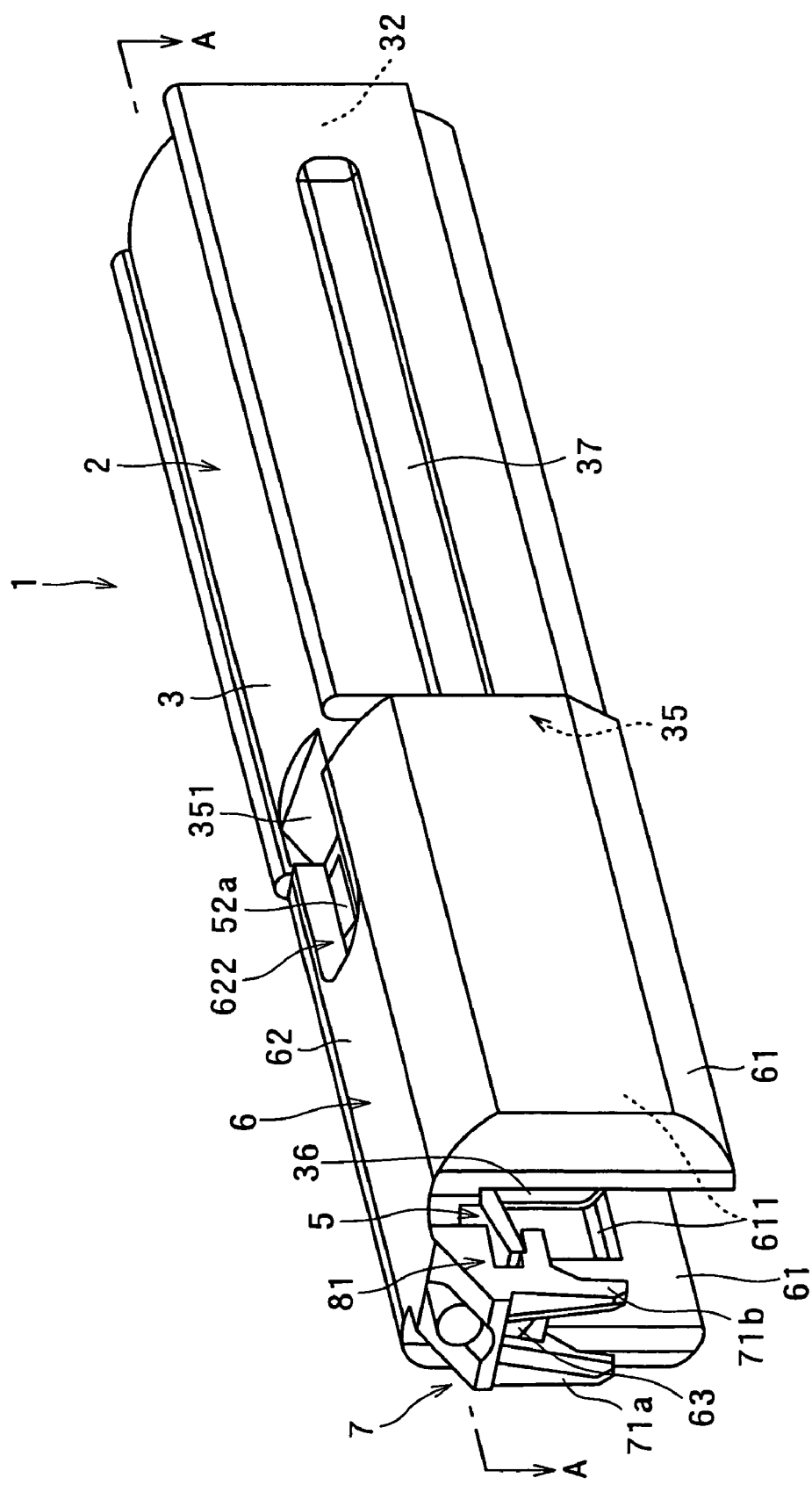
FIG. 1 is a perspective view showing the body fluid collecting device according to the first embodiment of the present invention.
Figure 2:
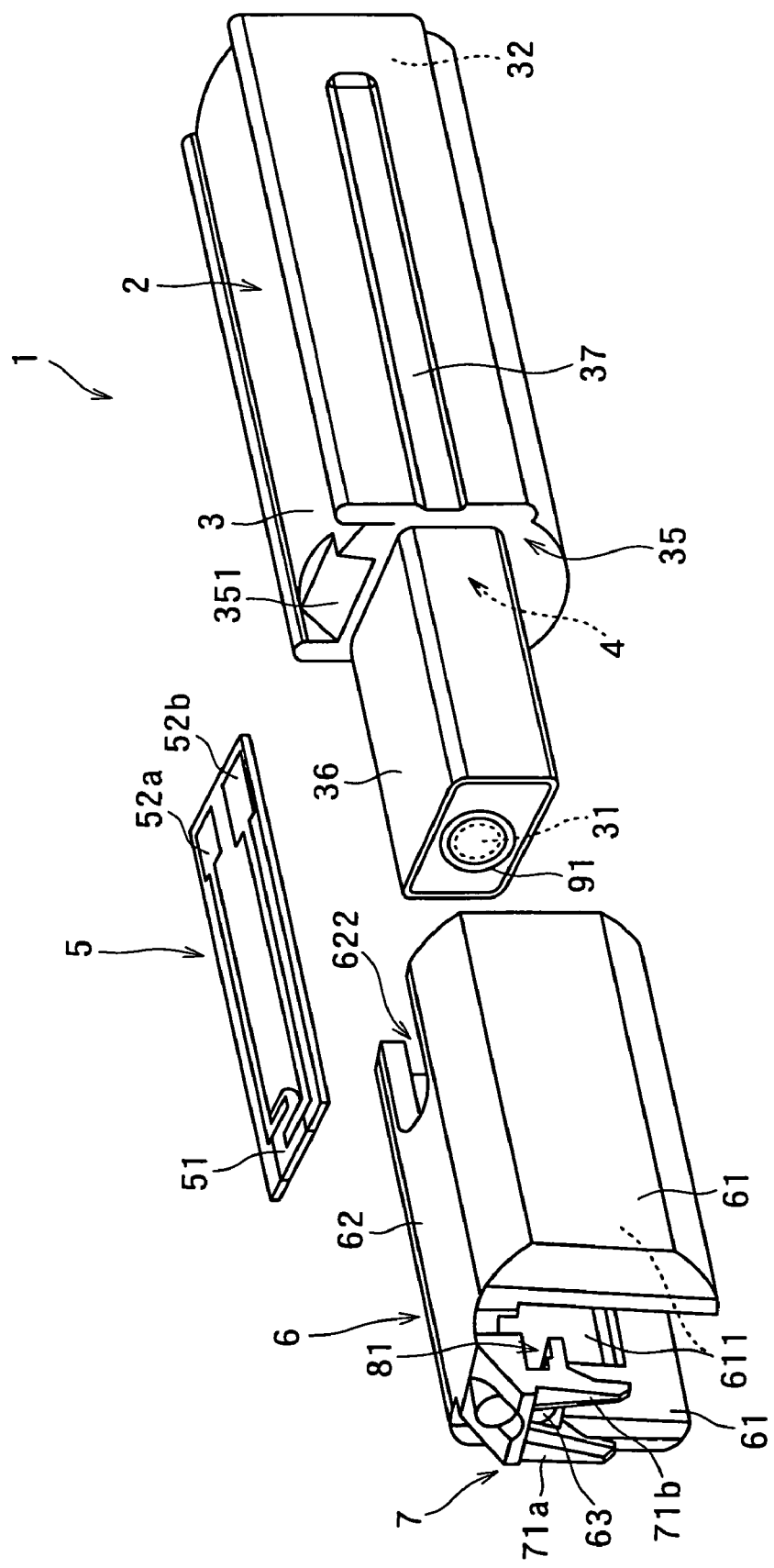
FIG. 2 is an exploded perspective view of the body fluid collecting device shown in FIG. 1.
Figure 3:
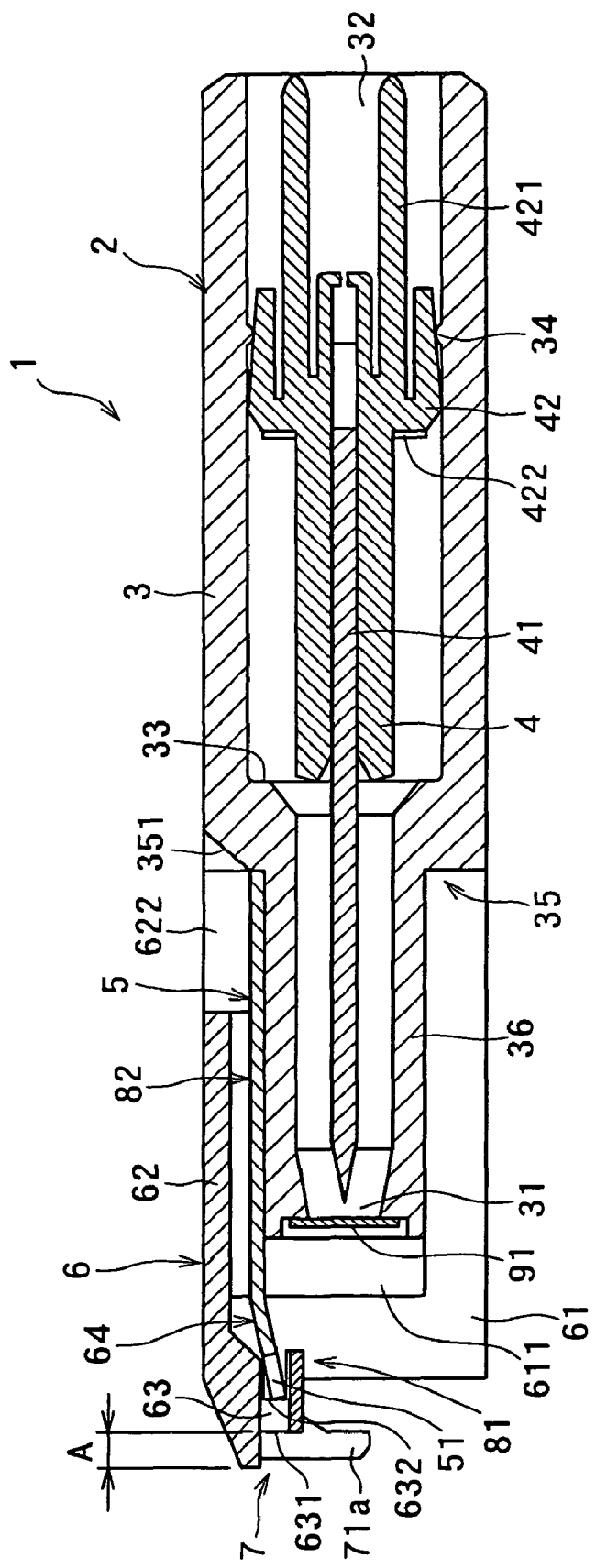
FIG. 3 is a sectional view taken along the line A-A in FIG. 1.
Figure 5:
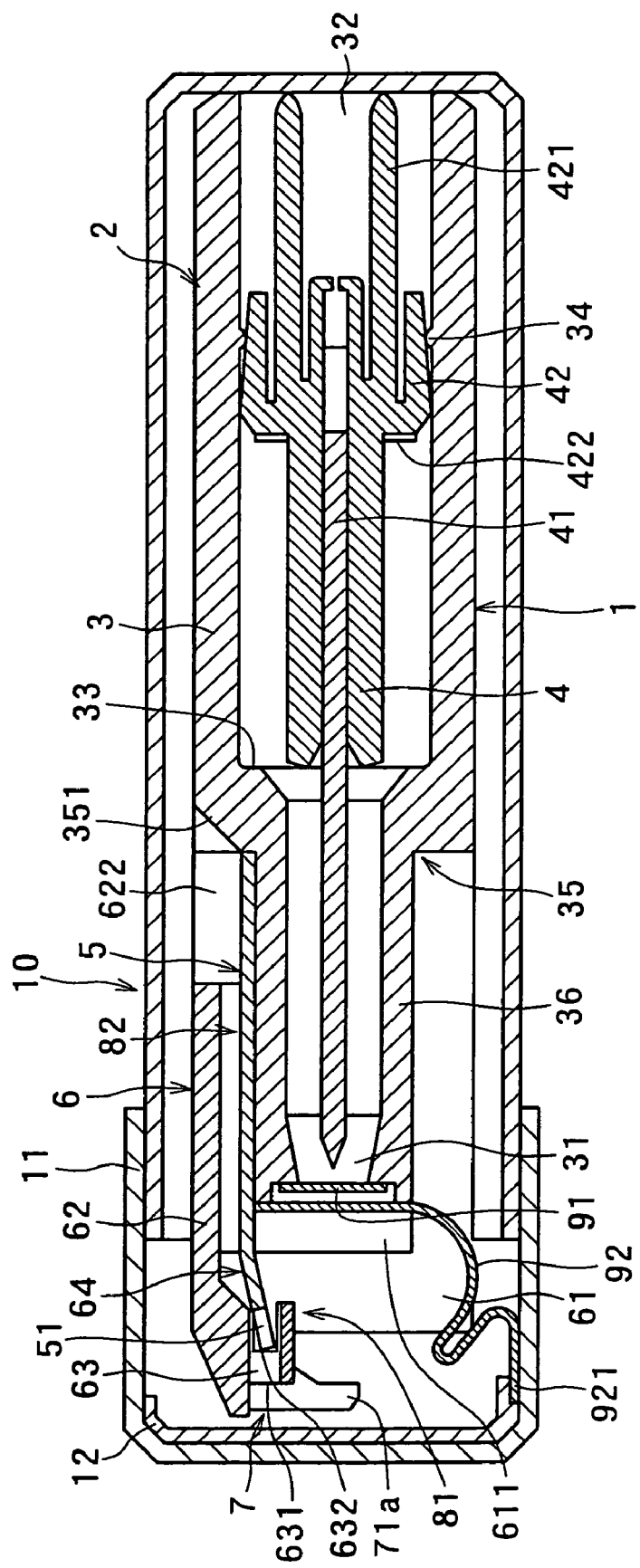
FIG. 5 is a longitudinal sectional view showing one example of the structure of the sealing member.
Figure 6:
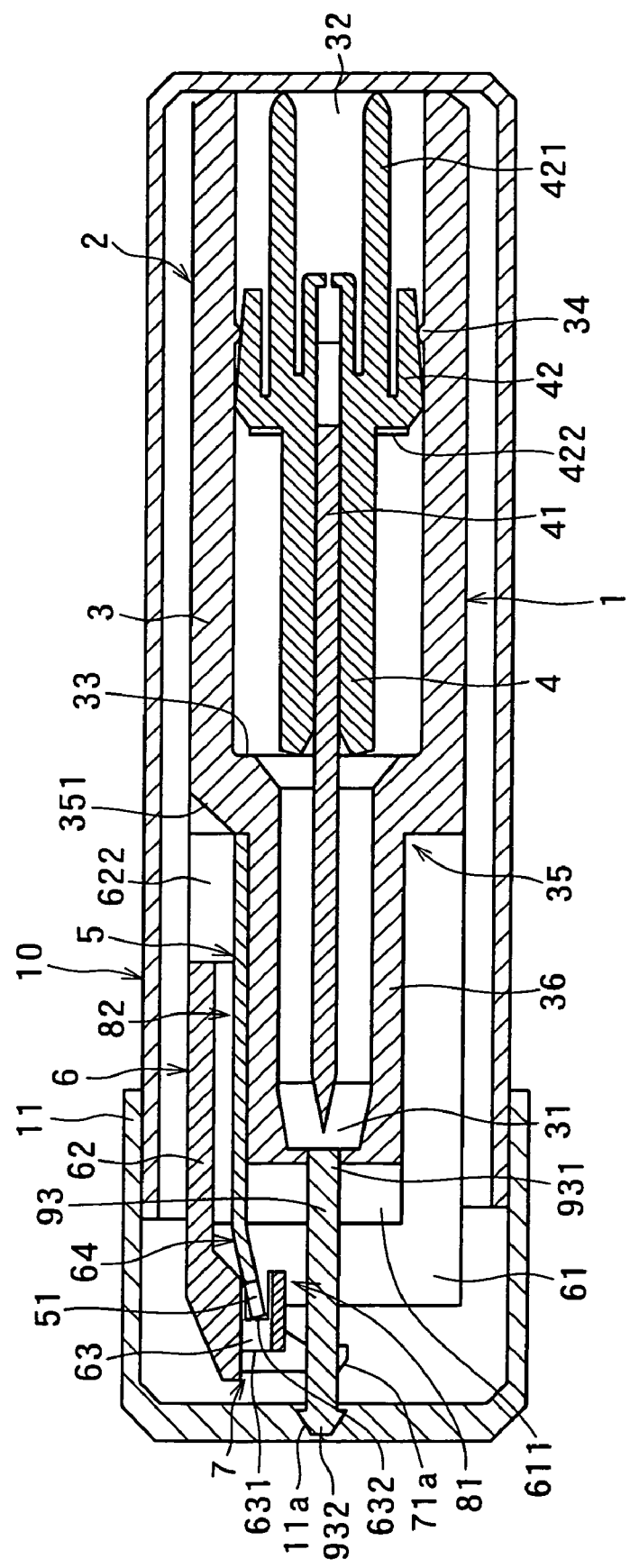
FIG. 6 is a longitudinal sectional view showing another example of the structure of the sealing member.

FIG. 1 is a perspective view showing the body fluid collecting device according to the first embodiment of the present invention. FIG. 2 is an exploded perspective view of the body fluid collecting device shown in FIG. 1. FIG. 3 is a sectional view taken along the line A-A in FIG. 1. FIG. 4 is a bottom view of the distal end of the sensor holder installed in the fluid body collecting device shown in FIG. 1. FIGS. 5 and 6 are longitudinal sectional views showing the examples of structure of the sealing member. Incidentally, conventions are adopted as follows in the following description. "Proximal end", "distal end", up and "down" represent respectively the right side, the left side, the upper side, and the lower side.

The body fluid collecting device 1 shown in FIG. 1 and other has a needle accommodating part 2, a sensor 5, and a sensor holder 6.

Descriptions will be made sequentially of the constituents of the body fluid collecting device 1.

The needle accommodating section (sticking needle unit) 2 includes the casing 3 and the sticking needle 4 which is accommodated in the casing 3 such that it can move in the axial direction.

The sticking needle 4 has a needle body 41 and a hub 42 fixed to the proximal end of the needle body 41.

The needle body 41 is a hollow or solid member made of a metallic material, such as stainless steel, aluminum, aluminum alloy, titanium, and titanium alloy. It has a sharp needle point, which sticks into the skin of the fingertip F, thereby causing the blood to bleed.

To the proximal end of the needle body 41 is fixed the hub 42 by welding, bonding (with an adhesive), fitting, or staking.

The hub 42 is an approximately cylindrical member, with its outer surface sliding on the inside of the casing 3.

At the proximal end of the hub 42 is formed a fitting part 421, which fits into the needle holder 411 of the plunger 410 (sticking means 400) when the body fluid collecting device 1 is mounted on the component measuring apparatus 100.

The casing 3 is a cylindrical member having an opening 31 at its distal end and an opening 32 at its proximal end. The needle body 41 passes through the distal opening 31 to project from the distal end of the body fluid collecting device 1.

The casing 3 has a decreased inside diameter in its distal part, so that the end surface 422 of the hub 42 comes into contact with the inside surface 33 as the sticking needle 4 moves in the distal direction. This structure regulates the maximum length of projection of the needle body 41 from the distal end of the body fluid collecting device 1. Thus, the needle point of the needle body 41 does not stick the fingertip F deeper than necessary when the sticking needle 4 sticks the surface of the fingertip F.

On the other hand, the casing 3 has an approximately constant inside diameter in its part close to the proximal end, and is slightly larger than the maximum outside diameter of the hub 42. This structure permits the sticking needle 4 to move smoothly in the axial direction of the housing 3.

The casing 3 has on its inside (close to the proximal end) a ring-shaped ridge 34 projecting inward. The ridge 34 engages with the outer periphery of the hub 42 when the body fluid collecting device 1 is not in use (as shown in FIG. 3), so that the sticking needle 4 is fixed to the casing 3. In this state, the needle point of the needle body 41 does not project from the distal opening 31.

The hub 42 fits into the ridge 34 with an adequate force which is strong enough for the fitting part 421 of the sticking needle 4 to smoothly fit into the needle holder 411 but weak enough for the hub 42 to easily disengage from the ridge 34 when the sticking means 400 is actuated.

Incidentally, there are no restrictions in the method of fixing the hub 42 to the casing 3. Other methods may be used, for example, by attaching engaging means to the inside of the casing 3 and/or the outside of the hub 42; by using friction between the inside of the casing 3 and the outside of the hub 42; by weakly bonding or welding together the casing 3 and the hub 42.

The fitting between the hub 42 and the inside undercut (or the ridge 34) of the casing 3 blocks entrance of bacteria into the needle accommodating section 2. Therefore, the sticking needle 4 remains sterilized until the body fluid collecting device 1 is used once the needle accommodating section 2 is sterilized.

There is a step 35 on the outside of the casing 3 at an intermediate point in the lengthwise direction. The sensor holder 6 is fitted to the part (fitting part 36) extending distally from this step 35. When the sensor holder 6 is fitted to the fitting part 36 (as shown in FIGS. 1 and 3), the proximal end of the sensor holder 6 comes into contact with the step 35, so that the sensor holder 6 is properly positioned (in the lengthwise direction) with respect to the casing 3 (the needle accommodating section 2). In other words, the step 35 determines the position of the sensor holder 6 (in the lengthwise direction) with respect to the needle accommodating section 2. The state as shown in FIGS. 1 and 3 is referred to as "the assembled state of the body fluid collecting device 1".

The position determining means mentioned above accurately controls how far the needle body 41 projects from the body fluid collecting device 1, thereby preventing the needle from sticking into the fingertip unnecessarily deep.

There are a pair of grooves 37 (facing each other) extending in the lengthwise direction on the outside of the casing 3. These grooves 37 function as nonslip means when a user grips the body fluid collecting device 1, so help the user to firmly grip the body fluid collecting device 1 by fingers.

The sensor 5 is intended to determine specific components in blood. In other words, upon contact with blood (or body fluid), it electrically measures (or detects) the blood glucose level.

In this embodiment, the sensor 5 should preferably be made of plastics, such as polyethylene terephthalate and polystyrene, so that it bends or curves in the non-contact space 64 mentioned later. The sensor 5 has, at the center of the distal end, a measuring part 51 which is 0.5 to 4.0 mm wide, 1.0 to 10.0 mm long, and 0.01 to 1.0 mm thick. The measuring part 51 is so constructed as to hold therein blood (body fluid) by capillary phenomenon, and it contains reagents to react with glucose (prescribed component) in blood.

The sensor 5 also has, on its upper-side, a pair of electrodes 52a and 52b in the form of thin film, as shown in FIG. 2. These electrodes have their distal ends positioned on the measuring part 51.

When the body fluid collecting device 1 is mounted on the component measuring apparatus 100, the contact points 731 and 732 of the measuring means 700 are in contact with (and electrically connected to) the electrodes 52a and 52b, respectively, so that voltage is applied to the measuring part 51 through the electrodes 52a and 52b.

The reagents used for determination include at least one species of oxidoreductases (such as glucose oxidase and glucose dehydrogenase) and at least one species of electron acceptors (such as potassium ferricyanide, ferrocene derivative, quinone derivatives, and metal complexes).

The determination of blood glucose level is based on the principle which is explained in the following. It is assumed that the reagent used for determination is a combination of glucose oxidase (GOD) and potassium ferricyanide ($K_3[Fe_{(III)}(CN)_6]$).

When blood enters the measuring part 51, glucose in the blood specifically reacts with GOD to evolve gluconic acid and electrons. Then, these electrons convert (reduce) the potassium ferricyanide ($K_3[Fe_{(III)}(CN)_6]$) into potassium ferrocyanide ($K_4[Fe_{(II)}(CN)_6]$). The potassium ferrocyanide is restored (oxidized) again to potassium ferricyanide by voltage applied from the measuring means 700. At this time, current occurs. The amount of this current is proportional to the amount of glucose; therefore, it is possible to calculate the blood glucose level by measuring (detecting) the change in current from the sensor 5 with the help of the measuring means 700.

The sensor 5 mentioned above is held between the needle accommodating part 2 and the sensor holder 6. The sensor holder 6 is mounted on the distal end of the needle accommodating part 2. (The distal end is the mounting part 36 of the casing 3.) The sensor holder 6 has a pair of side walls 61 and 61 facing each other and a top plate 62 (which connects the side walls and has a U-shaped cross section).

On the inside of each side wall 61 is formed a groove 611 extending in the lengthwise direction. When the body fluid collecting device 1 is assembled, both sides of the mounting part 36 of the casing 3 fit into these grooves 611, so that the sensor holder 6 is fixed to the needle accommodating part 2.

The sensor holder 6 and the casing 3 (the needle accommodating part 2) are in contact with each other through flat surfaces, so that the flat sensor 5 is held (supported) stably and firmly.

In addition, when the body fluid collecting device 1 is assembled, the proximal end of the sensor 5 is held between the top of the mounting part 36 of the casing 3 and the inside (or the lower side) 621 of the top plate 62. This simple structure firmly fixes the sensor 5, and hence the body fluid collecting device 1 can be assembled very easily. In this embodiment (in which the body fluid collecting device has the sticking needle integral therewith), there is a second supporter 82 that supports the proximal end of the sensor 5. Inside the distal end of the sensor holder 6 is a first supporter 81 that supports the vicinity of the measuring part 51 of the sensor 5.

In other words, the body fluid collecting device 1 has a first supporter 81 (which supports the vicinity of the measuring part 51 of the sensor 5) and a second supporter 82 (which supports the sensor 5 at its part closer to the proximal side than the first supporter 81).

At the distal end of the sensor holder 6 is formed a blood (body fluid) duct 63 communicating with the first supporter 81. This blood duct 63 collects blood bleeding from the fingertip F at which the sticking needle 4 has been stuck, and then it introduces the collected blood to the distal end (the measuring part 51) of the sensor 5 supported by the first supporter 81.

The blood duct 63 is a thin orifice, which has an opening 631 at its distal end (from which blood enters) and an opening 632 at its proximal end (from which blood leaves). Blood is fed to the measuring part 51 through the blood duct 63 by capillary phenomenon.

The blood duct 63 that relies on capillary phenomenon should have adequate dimensions (especially, an adequate ratio of length to inside diameter).

To be concrete, the length (indicated by L in FIG. 4) of the blood duct 63 should be about 0.1 to 10 mm, preferably about 0.5 to 5 mm, although it is not specifically restricted. Also, the inside diameter (indicated by D in FIG. 4) should be about 0.1 to 3 mm, preferably about 0.5 to 1.5 mm, although it is not specifically restricted.

The volume of the blood duct 63 should be about 0.5 to 2 times, preferably 0.8 to 1.5 times, the volume of the measuring part 51 of the sensor 5, although it is not specifically restricted. Specifying the volume of the blood duct 63 based on the volume of the measuring part 51 makes it possible to reduce the amount of blood to be collected. As the result, the amount of bleeding from the stuck point of the fingertip F is reduced and hence the patient's strain is also reduced. Moreover, if the amount of blood is not enough to fill the blood duct 63, blood does not come into contact with the measuring part 51. This avoids failure in measurement due to insufficient blood sample.

The first supporter 81 mentioned above is placed nearer the central axis of the sticking needle 4 than the second supporter 82 mentioned above. The advantage of arranging the first and second supporters 81 and 82 in this manner is that the sensor 5 is bent or curved in the non-contact space 64 mentioned later (which is between the first supporter 81 and the second supporter 82). In other words, the distal end of the sensor 5 is bent (or inclined) toward the central axis of the sticking needle 4, and hence the measuring part 51 of the sensor 5 is arranged aslant with respect to the lengthwise direction of the blood duct 63. Moreover, with the distal end of the sensor 5 bent or inclined toward the central axis of the sticking needle 4, the sensor 5 is firmly fixed by the first and second supporters 81 and 82, and the distal end of the sensor 5 is brought close to the sticking position.

Also, as mentioned above, the vicinity of the measuring part 51 of the sensor 5 is supported by the first supporter 81 and the measuring part 51 is placed near the vicinity of the opening 632 (for outlet) of the blood duct 63.

Arrangement in this manner offers the advantage that the blood introduced through the blood duct 63 is efficiently fed into the measuring part 51 and hence the blood glucose level can be measured with a less amount of blood sample.

Especially, the body fluid collecting device 1 mentioned above has a non-contact space 64 (in which the surface of the sensor 5 does not come into contact with the inside of the sensor holder 6) between the first supporter 81 and the second supporter 82. The volume of the non-contact space 64 is larger than that of the space demarcated by the first supporter 81. Thus, the blood introduced through the blood duct 63 by capillary phenomenon reaches the first supporter 81 but its movement toward the proximal end is prevented. As the result, the collected blood stays in the first supporter 81 and is supplied to the measuring part 51 efficiently (without waste). This leads to reduction in the amount of blood to be collected.

In this embodiment, the non-contact space 64 prevents blood (body fluid) from infiltrating into any other part than the measuring part 51 of the sensor 5.

In addition, above the proximal end of the first supporter 81 is formed a concave 811 that communicates with the non-contact space 64. In this embodiment, this concave 811 is formed by partly cutting out the first supporter 81, as shown in FIG. 4. The concave (notch) 811 certainly prevents blood from infiltrating into the proximal end of the sensor 5 along the upper lateral side of the sensor 5.

Incidentally, the means to prevent infiltration of blood (or body fluid) does not necessarily to be the non-contact space 64 formed between the first supporter 81 and the second supporter 82. The same object will be achieved by making water-repellent the vicinity of the proximal end of the first supporter 81.

At the end of the sensor holder 6 is formed a guide 7 (which projects from the end). This guide 7 efficiently introduces blood into the opening (inlet) 631 of the blood duct 63. It has a plurality of legs. (Two legs 71a and 71b are shown in FIG. 4.)

The legs 71a and 71b extend from the vicinity of the opening (inlet) 631 of the blood duct 63 toward the central axis of the sticking needle 4. In addition, the legs 71a and 71b gradually separate from each other as they extend toward the central axis.

In other words, the legs 71a and 71b are so arranged as to incline inward, but they do not join together at their lower ends (as shown in FIG. 1). Therefore, they do not clog the blood duct 63 (or the internal space of the guide 7) when the distal end of the guide 7 is brought into contact with the skin of the fingertip F for blood collection. That is, they secure the passage for blood, thereby ensuring smooth supply of blood to the measuring part 51.

Incidentally, the number of legs is not limited to the one shown in the figure; it may be three or more.

The distance from the distal end of the guide 7 to the opening (inlet) 631 of the blood duct 63 should preferably be about 0.1 to 10 mm, more preferably about 0.2 to 3 mm. (The distance is indicated by "A" in FIG. 3.) The thus specified length (A) is necessary for a small amount of blood to be introduced efficiently into the opening (inlet) 631 of the blood duct 63.

The guide 7 should preferably be hydrophilicized, so that it rapidly introduces blood into the opening (inlet) 631 of the blood duct 63.

Hydrophilicizing may be accomplished by physical activation such as ozone treatment, plasma treatment, glow discharge, corona discharge, and UV light irradiation, or by chemical coating with any of surfactant, water-soluble silicone, hydroxypropyl cellulose, polyethylene glycol, polypropylene glycol, and the like.

Alternatively, the guide 7 itself may be formed from a highly hydrophilic material such as acrylic resin.

Such hydrophilicizing as mentioned above may also be applied to other parts (e.g., the inside of the first supporter 81) of the body fluid collecting device 1.

The sensor holder 6 (or the body fluid collecting device 1) has its distal end made substantially transparent (colorless, colored, or translucent), so that the user (or patient) can watch (from outside of the body fluid collecting device 1) blood being fed to the measuring part 51 through the blood duct 63. This permits the user (or patient) to feel easy. Moreover, in this way it is possible to avoid failure in measurements (or incorrect measurement) due to insufficient blood collection (or malfunction of blood introduction into the blood duct 63).

The sensor holder 6 (or the top plate 62) has a notch 622 formed at its proximal end. When the body fluid collecting device 1 is assembled, the notch 622 permits the proximal end of the electrodes 52a and 52b of the sensor 5 to be exposed to the outside of the body fluid collecting device 1.

When the body fluid collecting device 1 is mounted on the component measuring apparatus 100 (or the housing 500), the contact points 731 and 732 advances into the notch 622, so that a part of their vertices come into contact with the electrodes 52a and 52b.

The step 35 of the needle accommodating part 2 (or the casing 3) has an inclined plane 351 formed at the position corresponding to the notch 622. The inclined plane 351 permits the contact points 731 and 732 to advance into and retract from the notch 622 smoothly when the body fluid collecting device 1 is mounted and dismounted on and from the component measuring apparatus 100.

The sensor holder 6, casing 3, and hub 42 mentioned above should preferably be made of plastics. Examples of the plastics include ABS resin, AS resin, polyethylene, polypropylene, polystyrene, polyvinyl chloride, polyvinylidene chloride resin, polyphenylene oxide, thermoplastic polyurethane, polymethyl methacrylate, polyoxyethylene, fluorocarbon resin, polycarbonate, polyamide, acetal resin, acrylic resin, polyethylene terephthalate, and other thermoplastic resins (which are capable of injection molding), and phenolic resin, epoxy resin, silicone resin, unsaturated polyester resin, and other thermosetting resins.

The body fluid collecting device 1 is assembled after the needle accommodating part 2 has been sterilized with ethylene oxide gas (EOG) or the like. In this embodiment, the needle accommodating part 2 is sterilized after sealing the distal opening 31 of the casing 3 with a membrane 91 which permits gas permeation but prevents the passage of bacteria.

In the proximal part of the needle accommodating part 2 before the body fluid collecting device 1 is in use, the peripheral part of the hub 42 fits into the ridge 34 and the sticking needle 4 is fixed to the casing 3, as mentioned above. The fitting part allows the passage of gas to a certain degree but prevents the passage of bacteria. Therefore, if the distal opening 31 of the casing 3 is sealed with a membrane (filter) 91 and then sterilization is performed, the inside of the needle accommodating part 2 remains sterilized until the body fluid collecting device 1 is put to use.

The membrane 91 (as shown in FIG. 3) is unsealed as it is pierced by the needle point of the needle body 41 when the sticking needle 4 sticks the fingertip F.

The sealing member may be constructed differently as explained later with reference to FIGS. 5 and 6.

The sealing member shown in FIG. 5 is the membrane 92, which is identical with the membrane mentioned above. It has one end 921 thereof fixed to the lid 11 of the case 10 which accommodates the body fluid collecting device 1. To be concrete, one end 921 of the membrane 92 is held (and fixed) between the lid 11 and the internal member 12 placed in the lid 11. Therefore, as soon as the lid 11 of the case 10 is removed, the membrane 92 peels off from the needle accommodating part 2 to open it.

The sealing member shown in FIG. 6 is the pin 93, with its one end 931 fitting into the distal opening 31 of the casing 3. FIG. 6 shows the body fluid collecting device 1 which has been assembled after sterilization of the needle accommodating part 2 with its end closed.

When the body fluid collecting device 1 is accommodated in the case 10, the fitting part 932, which is formed at another end of the pin 93, fits into the hole 11a which is formed inside the lid 11.

The lid 11 fits into the case 10 with a larger force than the pin 93 fits into the distal opening 31 of the casing 3. Therefore, as soon as the lid 11 is removed, the pin 93 releases itself from the needle accommodating part 2 to open it.

The body fluid collecting device 1 mentioned above assumes approximately a rectangular solid as shown in FIGS. 1 and 2. Therefore, it does not roll about on the table before and after its use, and there is no possibility of blood being scattered after blood collection.

When the body fluid collecting device 1 is mounted on the component measuring apparatus 100, its distal end projects from the apparatus 100 as shown in FIG. 10. To use it, the distal end of the guide 7 is brought into contact with the surface (skin) of the fingertip F and then the sticking needle 4 sticks the surface of the fingertip F. The body fluid collecting device 1 used in this manner permits the user to establish the reference position that regulates the depth the sticking needle 4 reaches when it sticks into the fingertip F (or the length over which the needle body 41 projects). By using the distal end of the body fluid collecting device 1 as the reference position in this manner, it is possible to ensure uniform sticking into the fingertip F by the sticking needle 4. The foregoing structure permits the sticking needle 4 to stick the fingertip F in the neighborhood of the guide 7. Thus the guide 7 captures blood advantageously.

In addition, since the body fluid collecting device 1 has the sticking needle 4 and the sensor 5, as mentioned above, it is capable of continuous operation: needle sticking, blood collection, blood supply to the sensor 5, and determination of components. This facilitates easy and rapid measurements of blood glucose level. Moreover, the component measuring apparatus 100 merely needs simple preparatory operation, and this facilitates periodic use or repeated use. The body fluid collecting device 1 mentioned above is suitable for measurements of blood glucose level by the patient oneself. It is simple in structure, inexpensive, and suitable for mass production. A description is given below of the method for using the body fluid collecting device 1 mounted on the component measuring apparatus 100.

[1] First, the body fluid collecting device 1 is mounted on (inserted into) the mounting part 530 of the housing 500 through the opening 212 of the casing 210, so that the fitting part 421 of the sticking needle 4 fits on the needle holder 411.

The body fluid collecting device 1 is pushed further toward the proximal end, so that the plunger 410 is moved toward the proximal end against the urging force of the coil spring 420. In the initial state, a part in the vicinity of the vertex of the locking part 413 is kept in contact with the inside of the housing 500 by the elastic force of the elastic piece 412. As soon as the locking part 413 reaches the position of the opening 570, it projects into the opening 570, as shown in FIG. 10. In this state, the locking part 413 is caught by the edge of the opening 570 even after the removal of force to press the plunger 410 toward the proximal end by the body fluid collecting device 1. Thus, the plunger 410 is kept from moving toward the distal end. In this state, the coil spring 420 is compressed. Now, the procedure for sticking and blood collection by the sticking means 400 is ready to start.

In this stage, the contact points 731 and 732 of the measuring means 700 advance into the notch 622 of the sensor holder 6, so that they come into contact with the electrodes 52a and 52b of the sensor 5, respectively. In this way the sensor 5 is electrically connected to the measuring means 700.

[2] Then, the power switch (not shown) is turned on, so that the component measuring apparatus 100 is activated for measuring operation.

[3] The patient presses his fingertip F against the distal end of the guide 7 (or the distal end of the body fluid collecting device 1), as shown in FIG. 10. While keeping this state, the patient depresses the control button 222 to activate the component measuring apparatus 100.

With the control button 222 depressed, the unlocking part 223 moves in the direction of arrow as shown in FIG. 10. It comes into contact with the locking part 413 and depresses it back into the internal space 520 of the housing 500. Thus, the locking part 413 is disengaged, and the plunger 410 is moved toward the distal end by the elastic force of the coil spring 420 (which has been compressed). The movement of the plunger 410 toward the distal end causes the sticking needle 4 to move toward the distal end, so that the needle point of the needle body 41 pierces the membrane 91, passes through the distal opening 31, projects from the distal end of the body fluid collecting device 1, and sticks into the skin of the fingertip F.

After that the coil spring 430 pushes back the plunger 410 toward the proximal end. The plunger 410 reciprocates (or repeatedly moves toward the distal end and toward the proximal) due to elastic force applied by the coil springs 420 and 430. It eventually comes to rest at a position where the force of the coil spring 420 balances with that of the coil spring 430. In this stage, the needle point of the needle body 41 is accommodated in the body fluid collecting device 1. In other words, the body fluid collecting device 1 is so designed as to prevent the needle point of the needle body 41 from projecting from its distal end while it is not in use. Thus, it is quite safe to use without possibility of inadvertent injury and infection to the skin.

[4] The component measuring apparatus 100, with the body fluid collecting device 1 mounted thereon, is placed on a desk temporarily. Using his fingers, the patient kneads that part of the fingertip F which has been stuck by the sticking needle 4 so as to assist bleeding.

This step, however, may be omitted unless it is necessary.

[5] Holding the component measuring apparatus 100 again, the patient brings the guide 7 of the body fluid collecting device 1 into contact with the blood forming a small drop at that part of the fingertip where the needle has been stuck in the step [4] mentioned above.

In this step, the guide 7 introduces the blood into the opening (inlet) 631 of the blood duct 63. The blood passes through the blood duct 63 and reaches the measuring part 51 of the sensor 5 due to capillary phenomenon.

In the measuring part 51, glucose in the blood reacts with the reagents, thereby generating electric current in proportion to the amount of glucose.

[6] The control means 111 measures, with the measuring means 700, the change in current from the sensor 5 and performs arithmetic operations according to the thus obtained data. After temperature and hematocrit corrections, it determines the blood glucose level.

The thus calculated blood glucose level is displayed on the display unit 112, so that the patient can know his own blood glucose level.

The foregoing procedure makes it possible to rapidly and surely collect blood necessary and sufficient for measurement and to accurately determine the blood glucose level (or the amount of a specific component in blood) with a less amount of blood.

Second Embodiment

The second embodiment of the present invention covers another body fluid collecting device which is integral with the sticking needle.

Figure 7:
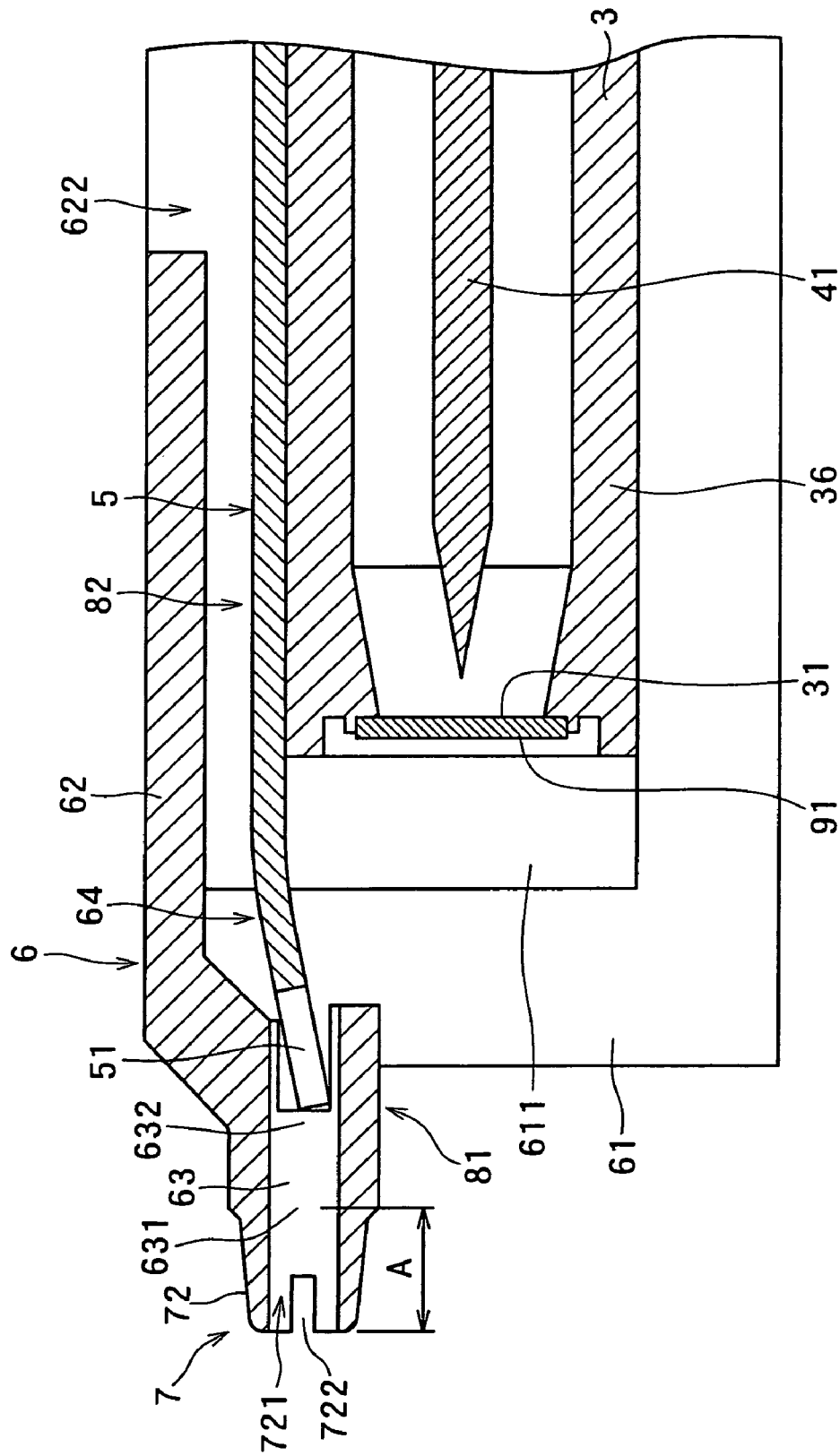
FIG. 7 is a longitudinal sectional view showing the structure of the tip of the body fluid collecting device according to the second embodiment of the present invention.

FIG. 7 is a longitudinal sectional view showing the distal end of the body fluid collecting device in the second embodiment of the present invention. Incidentally, the following conventions are adopted. "Proximal end" and "distal end" represent respectively the right side and the left side in FIG. 7.

The following describes the difference between the body fluid collecting device 1 in the second embodiment (shown in FIG. 7) and that in the first embodiment, without describing those items common to them.

The body fluid collecting device 1 in the second embodiment is identical with that in the first embodiment except that the guide 7 differs in shape.

In the second embodiment, the guide 7 consists of a capillary tube 72 having an internal space 721 communicating with the blood duct 63. The distal end of the guide 7 serves as a reference for contact with blood. It facilitate the step [5] mentioned above, while surely preventing the loss of blood which otherwise would occur because blood adheres to other parts than the guide 7 when the distal end of the guide 7 is brought into contact with the blood drop at the sticking point.

At the distal end of the capillary tube 72 is formed a groove 722 communicating with the internal space 721 (blood duct 63). The groove shown in FIG. 7 is a straight one extending in the radial direction of the capillary tube 72, and its both ends are open to the external periphery of the capillary tube 72.

The groove 722 prevents the internal space 721 of the capillary tube 72 (blood duct 63) from being clogged when the distal end of the capillary tube 72 (guide 7) is brought into contact with the skin of the fingertip F for blood collection, thereby ensuring the passage of blood and the smooth supply of blood to the blood measuring part 51.

The depth of the groove 722 varies depending on the surface state of the fingertip F without specific restrictions. However, it is usually no smaller than 0.1 mm, preferably from 0.2 to 1.8 mm. With an excessively shallow depth, the groove 722 will not permit blood to pass sufficiently through the internal space 721 when the distal end of the guide is strongly pressed against the skin of the fingertip F.

The groove 722 is not restricted in shape, number, and arrangement to the shown one. It may be constructed in such a way that when the distal end of the capillary tube 72 is brought into contact with the skin of the fingertip F, part of it remains free. In other words, more than one groove 722 (in an X-shaped pattern) radiating from the central axis of the capillary tube may be formed.

The body fluid collecting device constructed in this manner produces the same effect as that in the first embodiment.

Although the invention has been described in its preferred form (body fluid collecting devices illustrated above), it is to be understood that the invention is not limited to such specific embodiments but each constituent will be replaced by any one which produces the same effect. It goes without saying that the body fluid collecting device according to the present invention will fully produce its effect even though it is not provided with the sticking needle or the needle accommodating part.

To be concrete, the sticking needle used for the body fluid collecting device of the present invention may be replaced by another one (such as a syringe) for blood collection. Even in such a case, the present body fluid collecting device has the first supporter 81 and the second supporter 82 (which is closer to the proximal end than the first supporter 81) such that they form a non-contact space 64 between them in which the surface of the sensor 5 is substantially not in contact with the inside of the sensor holder 6, and the volume of the non-contact space 64 is larger than that of the space demarcated by the first supporter 81. Therefore, the blood reaches the first supporter 81 but does not move further toward the proximal end. Thus, the collected blood is retained in the first supporter 81 and then supplied to the measuring part 51 efficiently without any loss. This makes it possible to reduce the amount of blood to be collected.

In the one provided with the guide 7 and the blood duct 63, blood passes through the blood duct 63 due to capillary phenomenon and efficiently reaches the measuring part 51 which is aslant with respect to the lengthwise direction of the blood duct 63. This makes it possible to reduce the amount of blood to be collected.

According to the present invention, two or more constructions in the above-mentioned embodiments may be properly combined with each other.

The embodiments mentioned above are designed on the assumption that the body fluid to be collected is blood. However, the body fluid to be collected is not limited to blood. The body fluid may include urine, sweat, lymph, spinal fluid, bile, and saliva.

In addition, the embodiments mentioned above are designed on the assumption that the component to be determined is glucose (blood glucose level). However, the component for measurement is not limited to glucose; it includes, for example, alcohols, sugars, cholesterol, lactic acid, vitamins, hemoglobin, uric acid, creatinine, proteins, and inorganic ions (such as sodium).

The reagent in the sensor contains an oxidoreductase, which may be selected from alcohol oxidase, alcohol dehydrogenase, galactose oxidase, fructose dehydrogenase, cholesterol oxidase, cholesterol dehydrogenase, lactic acid oxidase, lactic acid dehydrogenase, ascorbic acid oxidase, bilirubin oxidase, and xanthine oxidase.

In the above-mentioned embodiments, the sensor is intended to determine the amount of specific components. However, it may also be intended for qualitative and/or quantitative analysis of specific components.

The sensor should preferably be so designed as to carry out analysis electrically by means of the above-mentioned reagents. However, analysis with an optical or any other means may also be adopted.

INDUSTRIAL APPLICABILITY

As mentioned above, the present invention produces the following effects.

The body fluid collecting device permits the user to collect body fluid easily and detects specific components in body fluid with a small amount of sample.

The body fluid collecting device is easy to assemble and is capable of easily controlling the depth of sticking. Moreover, it surely detects prescribed components in body fluid.

The body fluid collecting device is provided with a sticking needle so that it can perform in succession sticking, body fluid collection, supply of body fluid to the sensor, and detection of prescribed components. Therefore, it can easily and rapidly detect prescribed components. It can be easily made ready for use, which is advantageous for periodic use and repeated use.

The body fluid collecting device prevents inadvertent accidents, such as sticking twice the skin of the fingertip, and hence it is safe to use.

Therefore, the body fluid collecting device according to the present invention is suitable for determination of blood glucose level by the patient himself. It is simple in structure, inexpensive, and suitable for mass production.

What is claimed is:

1. A body fluid collecting device including a sensor to detect a prescribed component in the body fluid, wherein
    said sensor includes at its distal end a measuring part capable of holding said body fluid,
    said body fluid collecting device includes a first supporter to support the vicinity of said measuring part of said sensor and a second supporter to support said sensor at a place closer to the proximal end than said first supporter, with said first and second supporters forming between them a non-contact space in which the surface of said sensor does not substantially come into contact with the inside of said body fluid collecting device, and
    said first supporter has at its proximal end a concave that communicates with said non-contact space.

2. The body fluid collecting device as defined in claim 1, wherein said concave is a notch formed by cutting part of said first supporter.

3. The body fluid collecting device as defined in claim 1, wherein said sensor is bent or curved in said non-contact space.

4. The body fluid collecting device as defined in claim 1, wherein said first supporter is arranged closer to the central axis of said body fluid collecting device than said second supporter.

5. The body fluid collecting device as defined in claim 1, wherein said sensor electrically detects the prescribed component in the body fluid by contact with said body fluid.

6. The body fluid collecting device as defined in claim 1, which further includes a body fluid duct which communicates with said first supporter and introduces said body fluid into said measuring part.

7. The body fluid collecting device as defined in claim 6, wherein said body fluid duct has a volume which is 0.5 to 2 times the volume of said measuring part.

8. The body fluid collecting device as defined in claim 6, wherein said body fluid duct is 0.1 to 10 mm in length and 0.1 to 3 mm in inside diameter.

9. The body fluid collecting device as defined in claim 6, wherein said measuring part is inclined with respect to the lengthwise direction of said body fluid duct and is positioned in the vicinity of the outlet opening of said body fluid duct.

10. The body fluid collecting device as defined in claim 6, which further includes a guide that projects from the distal end of said body fluid collecting device and introduces said body fluid into the inlet opening of said body fluid duct,
    said guide being formed such that the distance from the distal end thereof to the inlet opening of said body fluid duct is 1 to 10 mm.

* * * * *

UNITED STATES PATENT AND TRADEMARK OFFICE
CERTIFICATE OF CORRECTION

| | | |
|---|---|---|
| PATENT NO. | : 7,771,368 B2 | |
| APPLICATION NO. | : 10/519790 | |
| DATED | : August 10, 2010 | |
| INVENTOR(S) | : Toshihisa Nakamura et al. | |

It is certified that error appears in the above-identified patent and that said Letters Patent is hereby corrected as shown below:

In column 7, line 50, the word "up" should be in quotes (i.e., up should be "up").

Signed and Sealed this
Fifteenth Day of March, 2011

David J. Kappos
*Director of the United States Patent and Trademark Office*